US005378368A

United States Patent [19]
Gill

[11] Patent Number: 5,378,368
[45] Date of Patent: * Jan. 3, 1995

[54] CONTROLLING SILICA/SILICATE DEPOSITION USING POLYETHER POLYAMINO METHYLENE PHOSPHONATES

[75] Inventor: Jasbir S. Gill, McKees Rocks, Pa.

[73] Assignee: Calgon Corporation, Pittsburgh, Pa.

[*] Notice: The portion of the term of this patent subsequent to Apr. 5, 2011 has been disclaimed.

[21] Appl. No.: 926,535

[22] Filed: Aug. 5, 1992

[51] Int. Cl.[6] .................................................. C02F 5/14
[52] U.S. Cl. ................................. 210/639; 210/700; 210/701; 252/180
[58] Field of Search .......................... 210/698–701, 210/639; 252/180, 181

[56] References Cited

U.S. PATENT DOCUMENTS

| | | | |
|---|---|---|---|
| 3,928,196 | 12/1975 | Persinski et al. | 252/180 |
| 4,080,375 | 3/1978 | Quinlan | 210/700 |
| 4,432,879 | 2/1984 | Greaves et al. | 210/699 |
| 4,510,059 | 4/1985 | Amjad et al. | 210/701 |
| 4,532,047 | 7/1985 | Dubin | 210/698 |
| 4,584,104 | 4/1986 | Dubin | 210/696 |
| 4,618,448 | 10/1986 | Cha et al. | 252/180 |
| 4,640,793 | 2/1987 | Persinski et al. | 210/698 |
| 4,874,527 | 10/1989 | Gill | 210/700 |
| 4,931,189 | 6/1990 | Dhawan et al. | 210/700 |
| 4,933,090 | 6/1990 | Gill et al. | 210/700 |
| 5,078,879 | 1/1992 | Gill et al. | 210/699 |
| 5,078,891 | 1/1992 | Sherwood et al. | 210/699 |
| 5,087,376 | 2/1992 | Bendiksen et al. | 210/700 |
| 5,158,685 | 10/1992 | Freese | 210/699 |

OTHER PUBLICATIONS

"Harrar, J. E. et al., Final Report on Tests of Proprietary Chemical Additives as Anti-Scalants for Hypersaline Geothermal Brine" Jan. 1980.

Harrar, J. E. et al., On Line Tests of Organic Additives for the Inhibition of the Precipitation of Silica from Hypersaline Geothermal Brine IV.

Harrar, J. E. et al., Studies of Scale Formation & Scale Inhibition at the Salton Sea Geothermal Field 1980.

*Primary Examiner*—Peter A. Hruskoci
*Attorney, Agent, or Firm*—Craig G. Cochenour; William C. Mitchell; Michael J. Kline

[57] ABSTRACT

Polyether polyamino methylene phosphonates, when added to various industrial water systems in concentrations between 0.1 mg/L and 50 mg/L, control silica/silicate deposition. In particular, this stabilization can be achieved under severe conditions which include elevated pH, high dissolved solids content, and high saturation levels of calcium carbonate.

8 Claims, No Drawings

CONTROLLING SILICA/SILICATE DEPOSITION USING POLYETHER POLYAMINO METHYLENE PHOSPHONATES

REFERENCE TO RELATED APPLICATIONS

Application Ser. No. 926,111, filed August 1992, involving a different inventive entity than that of the instant application, relates to compositions and methods for controlling silica/silicate deposition which utilize the same polyether polyamino methylene phosphonates, optionally in combination with certain polymers, as are employed in the compositions and methods of the instant application. The latter, however, does not employ any additional components, such as are disclosed in the former.

BACKGROUND OF THE INVENTION

1. Field of the Invention

The deposition of silica and various silicate salts in a variety of aqueous systems has long been a problem. These systems include, e.g., boilers and cooling towers. For the latter, the efficiency of the cooling system is often directly limited by high silica content of the water in many regions of the world, especially the western United States and Mexico, where surface and well waters have silica levels as high as 100 mg/L. It has recently been discovered that such silica and silicate salt deposits can also become a substantial problem in cooling towers in which the recirculating water has gone through a number of cycles, i.e., has been "cycled up". The formation of silica/silicate deposits may actually limit the number of such cycles to 2 or 3, thus imposing unsatisfactory restraints in areas where limited water supplies are a severe problem, or where waste treatment of large volumes of water has drawbacks. Also, in such cycled up cooling towers, the water is characterized by high pH and high calcite concentration. In aqueous systems having such severe conditions, not only are conventional agents for the control of calcium carbonate scale frequently unsuccessful in controlling such calcite scale deposits, but in a similar fashion, conventional agents for the control of silica and silicate salt deposits have no predictable or expected utility.

Silica (silicon dioxide) appears naturally in a number of crystalline and amorphous forms, all of which are water insoluble, thus leading to the formation of intractable deposits. Silicates are salts derived from silica or the silicic acids, especially orthosilicates and metasilicates, which may combine to form polysilicates. All of these, except the alkali silicates, are water insoluble Magnesium silicate in particular is prevalent and has limited water solubility. A number of different forms of silica and silicate salt deposits are possible, and these will depend, among other factors, on temperature, pH and the concentration/ratio of calcium and magnesium in the make-up water.

Traditionally, deposition has been controlled by softening the makeup water to the system being treated, by blowdown, or by both. If deposition does occur, however, because the silica scale is so tenacious and hard to remove, it will often be necessary to use both mechanical removal and washing with ammonium fluoride or hyudrofluoric acid in order to effectively remove the scale deposits. The use of agents for the control of silica and silicate deposition, such as those of the present invention, provide the advantage of avoiding such mechanical and chemical cleaning, which causes down time and increased energy and labor costs.

As already noted, the polyether phosphonates of the present invention are useful for controlling the deposition of silica and silicates under severe conditions which include elevated pH; and so it should be noted that pH affects the ionization of silanol groups and, therefore, affects the polymerization rate. Silica first forms, then three-dimensional networks form. Eventually, colloidal particles grow through condensation. At pH 7, nuclei formation and particle growth is very rapid. The pH of cycled up cooling towers is usually at least 8.5 or higher.

The polyether polyamino methylene phosphonates, when used in accordance with the method of the present invention, can prevent the deposition of silica and silicate salts. This method is especially useful under conditions of high pH and high calcite concentrations, e.g., those found in cycled up cooling towers. Various industrial and commercial water-carrying systems are subject to silica and silicate deposit formation problems. These deposits form frequently in the tubes of heat exchangers and on other heat exchange surfaces, such as those in cooling towers. Particular systems or applications areas where severe conditions, especially high alkalinity, lead to buildup of silica and silicate deposits, in addition to cycled up cooling towers, include reverse osmosis systems, sugar refining evaporators, and certain types of gas scrubbers.

The polyether polyamino methylene phosphonates used in the methods of the present invention, are usually used in threshold inhibitor amounts. The compositions of the present invention, especially those in which a polyether phosphonate is combined with a polymer, have dispersant properties as well and significantly reduce the adherency of any deposits which are formed, facilitating their easy removal.

Particular problems are encountered when attempting to prevent deposits of silica and silicate salts under severe conditions, where conventional treatments do not provide complete control. Conventional treatment can be used to inhibit silica/silicate deposits under normal conditions of alkalinity, e.g., up to 100 to 120 times calcite saturation, i.e., a water containing $Ca^{2+}$ and $CO_3^{2-}$ present at 100 times (100×) their solubility limit of calcium as calcite (calcite is the most common crystalline form of calcium carbonate). However, what is desired are inhibitors effective in greater than 150×water, especially in greater than 250×water, and more especially in greater than 300×water, i.e., where the calcite ions can be prevented from precipitating as calcium carbonate scale using substoichiometric amounts of an inhibitor. The polyether phosphonate compositions used in the methods of the present invention are especially useful under severe conditions characterized by a calcite saturation level of 150×and above, especially 250×and above, and more especially 300×and above, as defined in the paragraph immediately below.

Another characteristic feature of the severe conditions under which the polyether phosphonate compositions used in the methods of the present invention are especially useful is high pH, i.e. a pH of 8.5 and higher, particularly a pH of 9 or 10 or even higher.

One of the particular advantages of the polyether phosphonate compositions used in the methods of the present invention is the exceptional calcium tolerance which they exhibit. Calcium tolerance is a measure of a chemical compound's ability to remain soluble in the presence of calcium ions ($Ca^{2+}$). As pH increases, calcium tolerance decreases rapidly for many compounds which might be used to control silica/silicate deposits, and they precipitate with calcium at alkaline pH's, rendering them useless. While it is common practice to use an acid feed to the water of, e.g., a cooling tower system in order to lower pH and thus avoid the calcium tolerance problem, the danger to handlers which such acid feeding poses makes it all the more important to find inhibitors of silica/silicate deposits which operate at high pH's.

2. Brief Description of the Prior Art

It is known to use cationic polymers or cationic surfactants as silica scale inhibitors in hypersaline geothermal brines (Hatrat, J. E. et al., "Final Report on Tests of Proprietary Chemical Additives as Anti-scalants for Hypersaline Geothermal Brine", January 1980, Lawrence Livermore Laboratory, Harrar, J. E. et al., "On-Line Tests of Organic Additives for the Inhibition of the Precipitation of Silica from Hypersaline Geothermal Brine IV, Final Tests of Candidate Additives", February 1980. Lawrence Livermore Laboratories; and Hatrat, J. E. et al., "Studies of Scale Formation and Scale Inhibitors at the Salton Sea Geothermal Field", Corrosion/80. Paper No. 225, International Corrosion Forum, devoted exclusively to the Protection and Performance of Materials, Mar. 3-7, 1980. Chicago, Ill.

U.S. Pat. No. 4,933,090 discloses the use of phosphonates such as hexamethylene diamine tetra (methylene phosphonic acid) and diethylene triamine penta (methylene phosphonic acid) and anionic polymers to control silica deposition.

U.S. Pat. No. 3,928,196 discloses the use of copolymers of 2-acrylamido-2-methylpropysulfonic acid and acrylic acid as scale inhibitors.

U.S. Pat. No. 4,640,793 discloses the use of admixtures containing carboxylic acid/sulfonic acid polymers and phosphonates as scale and corrosion inhibitors.

U.S. Pat. No. 4,618,448 discloses the use of polymers comprising an unsaturated carboxylic acid, an unsaturated sulfonic acid and an unsaturated polyalkylene oxide as scale inhibitors.

Japanese No. 57-084794 discloses the use of copolymers of acrylic acid and allyl polyethylene glycol as scale inhibitors.

U.S. Pat. No. 4,510,059 discloses the use of carboxylic functional polyampholytes to reduce silica deposits in aqueous systems.

U.S. Pat. No. 4,432,879 discloses the use of 2-phosphonobutane-1,2,4-tricarboxylic acid and methacrylic acid/2-acrylamido-2-methylpropyl sulfonic acid polymers to disperse solid matter such as clay including China Clay ($Al_2O_3.2H_2O.2SiO_2$) in aqueous systems. Threshold inhibition of silica/silicates is not disclosed or suggested.

U.S. Pat. No. 4,532,047 discloses a method of inhibiting amorphous silica scale formation using polypolar organic compounds and borate ion sources.

U.S. Pat No. 4,584,104 discloses a method of inhibiting amorphous silica scale formation using a source of orthoborate ions.

U.S. Pat. No. 4,080,375 discloses methylene phosphonates of amino-terminated oxyalkylates for use as scale inhibitors, but these compositions are not the same as those used in the method of the present invention, nor is there any suggestion that such compositions would be useful for inhibiting the deposition of silica/silicates.

U.S. Pat. No. 4,931,189 discloses aminomethylene phosphonates of the type used in the method of the present invention, but for inhibiting oil field scale formation involving a high brine environment susceptible to gypsum or barite scale formation. Such use in no way suggests the inhibition of silica/silicate scale deposition described herein.

The polyether polyamino methylene phosphonates of the type which are used to inhibit silica/silicate scale deposition in the method of the present invention, are described in copending application Ser. No. 07/879,231, filed May 11, 1992 (Attorney Docket No. C-1527IA). While their use for the control of calcium carbonate scale under severe conditions which include elevated pH and high calcium carbonate saturation levels, is described, there is no suggestion of their use to inhibit silica/silicate scale deposition.

U.S. Pat. No. 4,874,527 discloses a method for controlling the formation of silica/silicate deposits in aqueous systems by adding an imine polymer, a phosphonate and, optionally, a source of moilybdate or borate ions to the aqueous system.

U.S. Pat. No. 5,078,879 discloses a method for controlling the formation of silica/silicate deposits by adding 2-phosphonobutane-1,2,4-tricarboxylic acid and, optionally, an anionic polymer.

SUMMARY OF THE INVENTION

The present invention relates to a method of inhibiting the deposition of silica and/or silicate salt scale in an aqueous system having a pH of at least 8.5 and a calcite saturation level of at least 150×, comprising the step of treating said system with an effective scale-inhibiting amount of a polyether polyamino methylene phosphonate of the following formula:

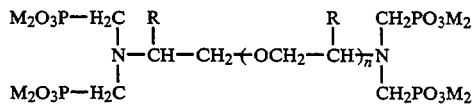

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl.

A preferred subclass of compositions of the above formula is that wherein M is hydrogen, R is methyl, and n is from about 2 to about 3, most preferably an average of about 2.6.

In particular, the present invention relates to such a treatment method in which the aqueous system being treated is characterized by the severe conditions of a pH of at least 9.0 or greater, and a calcite concentration of at least 250×, especially 300× or greater; and the polyether phosphonate is used in an amount sufficient to achieve a concentration of from 0.1 to 50 mg/L in said aqueous system, preferably from 1.0 to 10 mg/L, and most preferably from 2 to 5 mg/L.

The present invention further relates to a method of inhibiting the deposition of silica and/or silicate salt scale in an aqueous system having a pH of at least 8.5 and a calcite saturation level of at least 150×, comprising the step of treating said system with an effective scale-inhibiting amount of a composition comprising a polyether polyamino methylene phosphonate of the formula above, together with a polymer additive comprising one or more members selected from the group consisting of: homo- and copolymers including terpolymers comprising one or more of acrylamide (AM), acrylic acid (AA), 2-acrylamide-methyl propane sulfonic acid (AMPSA), methacrylic acid (MAA), iraconic acid (IA), polyethylene glycol monomethacrylate (PGM), maleic anhydride (MAH), maleic acid (MA), t-butyl acrylamide (TBAM), sodium styrene sulfonate (SSS), sodium vinyl sulfonate, hydroxy propyl acrylate, hydroxy propyl methacrylate, 3-allyloxy-2-hydroxy propane sulfonic acid, sodium salt (AHPS), and vinyl phosphonic acid, wherein the weight average molecular weight for such polymer additives is in the range of from about 500 to 250,000.

In particular, the present invention relates to such a method in which for the above formula for the polyether phosphonate, M is hydrogen, R is methyl, and n is from about 2 to about 3, most preferably an average of about 2.6; the aqueous system being treated is characterized by the severe conditions of a pH of at least 9.0 or greater, and a calcite concentration of at least 250×, especially 300× or greater; and the polyether phosphonate is used in an amount sufficient to achieve a concentration of from 0.1 to 50 mg/L in said aqueous system, preferably from 1.0 to 10 mg/L, and most preferably from 2 to 5 mg/L; and said polymer additive is a member selected from the group consisting essentially of 90/10 to 10/90 AA/AMPSA, preferably 75/25 and 60/40 AA/AMPSA, 100 AA, 75/25 SSS/MA, 33/33/34 AA/MAA/IA, 50/50 AA/AM, 70/20/10 AA/AMPSA/PGM-5 (having 5 repeating oxyethylene units), and AA/AMPSA/TBAM.

The present invention still further relates to a composition for inhibiting the deposition of silica and/or silicate salt scale in an aqueous system having a pH of at least 8.5 and a calcite saturation level of at least 150×, comprising a polyether polyamino methylene phosphonate of the formula above. The present invention also relates to a composition comprising a polyether phosphonate of the formula above in combination with a polymer additive which is a member selected from the group consisting essentially of those enumerated above. In particular, the present invention relates to such a composition in which for the above formula for the polyether phosphonate, M is hydrogen, R is methyl, and n is from about 2 to about 3, most preferably an average of about 2.6; and said polymer additive is a member selected from the group consisting essentially of 90/10 to 10/90 AA/AMPSA, preferably 75/25 and 60/40 AA/AMPSA, 100 AA, 75/25 SSS/MA, 33/33/34 AA/AA/IA, 50/50 AA/AM, 70/20/10 AA/AMPSA/PGM-5 (having 5 repeating oxyethylene units), and AA/AMPSA/TBAM.

DETAILED DESCRIPTION OF THE INVENTION

The active ingredient in the compositions and methods of the present invention for inhibiting the deposition of silica/silicate scale in an aqueous system, especially one characterized by severe conditions of high pH and high calcite concentration, is a polyether polyamino methylene phosphonate of the formula:

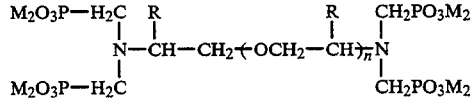

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl. A preferred subclass of compositions of the above formula is that wherein M is hydrogen, R is methyl, and n is from about 2 to about 3, most preferably an average of about 2.6.

In order to obtain high levels of control of silica/silicate deposits, especially under the severe conditions defined herein, it has been found that there are certain essential components of the structure of such polyether polyamino methylene phosphonate or N-oxides which are necessary to provide that performance. For example, the N,N-bis(phosphonomethyl)amino portion of the structure is essential. Whether this group is present initially in the phosphonic acid form or as an alkali metal or other salt of the acid, has no critical bearing on the performance of the overall molecule. At the pH's under which the phosphonate compositions function, they are, and must be, in their ionized form. Thus, it is not critical whether "M" is hydrogen or a suitable cation, and the selection of an appropriate salt form is well within the skill of the art. Alkali metal salts are the most simple, and are preferred for that reason. Overall, however, it is preferred that M is hydrogen.

The polyether polyamino methylene phosphonate may be in the N-oxide form: N→O. This group confers significant resistance to degradation by chlorine and bromine biocides, or mixtures thereof, which may be present in the aqueous system being treated, presumably by preventing oxidative attack on the nitrogen atom of the group.

A preferred structural feature of the polyether polyamino methylene phosphonates and N-oxides useful as deposit control agents is the isopropyl group which bridges the diphosphonomethylamino group and the polyether group. This group can also be an ethylene moiety.

Another structural element of the phosphonate silica/silicate deposit inhibitors is the polyether moiety. Since the polyether polyamino methylene phosphonates are prepared by phosphonomethylation of the appropriate diamine, the character of the polyether moiety will depend upon the way in which the amine starting material is made. Processes for making such polyether diamines are known in the art; and attention is directed particularly to U.S. Pat. No. 3,236,895, which describes preparation of a variety of polyether diamines especially useful in preparing the phosphonate final products used as deposit control agents in the present invention.

In accordance with the processes set out in U.S. Pat. No. 3,236,895 and related processes described in the prior art, it is possible to prepare any one of a number of desired polyether diamines within the scope of the present invention. In the general formula for the polyether polyamino methylene phosphonates used herein, the polyether moiety is simply represented by the formula:

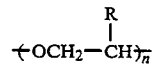

Since R may be hydrogen or methyl, both ethyleneoxy and propyleneoxy units are possible. Moreover, R is to be independently chosen, i.e., ethyleneoxy and propyleneoxy units may alternate in various patterns, including blocks of each, or they may be all one or the other. For example, the following are just some of the polyether segments which might be prepared to form the basis for the corresponding diamines, which would then be used to make phosphonates within the scope of the present invention (where EO= ethyleneoxy, and PO=propyleneoxy):

EO; PO; EO-EO; PO-PO; EO-PO; EO-EO-EO; PO-PO-PO; EO-EO-PO; EO-PO-PO; EO-PO-EO; PO-EO-PO; EO-EO-EO-EO; PO-PO-PO-PO; EO-PO-PO-PO; EO-EO-PO-PO; EO-EO-EO-PO; EO-PO-EO-PO; EO-PO-PO-EO; PO-EO-EO-PO

In the above examples, "n" in the main formula would be an integer of from 1 to 4. Since "n" is defined as being from 1 to 12, an even larger number of possible polyether moieties is included. However, it has been found that generally the polyether polyamino methylene phosphonates of lower molecular weight, i.e., where "n" is a smaller integer, are those which provide the greatest amount of scale inhibition under the severe conditions of high pH and high calcite concentration, and thus are those which are preferred. Examples of some of these preferred phosphonates are shown in the table below, where Z=methylenephosphonate:

$$Z_2-N-\overset{R_z}{\underset{|}{C}}HCH_2-(OCH_2\overset{R_a}{\underset{|}{C}}H)_a-(OCH_2\overset{R_b}{\underset{|}{C}}H)_b-NZ_2$$

| Id. No. | a | b | $R_z$ | $R_a$ | $R_b$ |
|---|---|---|---|---|---|
| A | 2 | 1 | $CH_3$ | H | $CH_3$ |
| B | 2.6* | 0 | $CH_3$ | $CH_3$ | — |
| C | 2 | 0 | $CH_3$ | $CH_3$ | — |
| D | 8.5* | 1 | $CH_3$ | H | $CH_3$ |
| E | 5.6* | 0 | $CH_3$ | $CH_3$ | — |
| F | 2 | 0 | H | H | — |
| G | 3 | 0 | H | H | — |
| H | 3 | 0 | $CH_3$ | $CH_3$ | — |
| I | 3 | 1 | H | $CH_3$ | H |
| J | 4 | 0 | H | $CH_3$ | — |

* = the value of "n" on average.

It will be noted from the table above that in several cases, "n" has an average value, i.e., the number of repeating ethyleneoxy or propyleneoxy units may vary. Thus, it is possible to have a mixture of varying chain lengths of polyoxyethylene or polyoxypropylene in the final product. This is also contemplated to be within the scope of the present invention, so long as the requirements with respect to the limit of "n" are observed. Consequently, while "n" is merely defined as an integer or fractional integer which is, or on average is, from about 2 to about 12, it has two aspects. It defines the total of the number of repeating ethyleneoxy and/or propyleneoxy units considered separately, and thus if "n" is, e.g., 4, it includes 4 propyleneoxy units, 3 propyleneoxy units and 1 ethyleneoxy unit, 2 propyleneoxy units and 2 ethyleneoxy units, and so forth. The value of "n" may also represent an average number, and this is always the case, of course, when it is a fractional integer. In this case, for each of the ethyleneoxy and/or propyleneoxy units considered separately, mixtures of these units may be present so as to give an average value for "n". For example, in the table above, for Id. No. D, the total of "a" and "b" is 9.5, which is the value of "n". What is described is a mixture of polyether phosphonates in which all of them have an isopropyl bridging group and an ethyleneoxy moiety, but the repeating propyleneoxy units are such that on average their value is about 8.5.

The number of repeating ethyleneoxy or oxypropylene units, designated by the subscript "n", determines the total molecular weight of the overall polyether polyamino methylene phosphonate or corresponding N-oxide, and thus plays a critical role in determining the scale inhibiting performance of that phosphonate. It has been found that in order to provide adequate scale control under the severe conditions of use defined herein, it is necessary that "n" be an integer or fractional integer which is, or on average is, from about 2 to about 12, inclusive.

As discussed above, the reason for "n" being potentially a fractional integer arises from the fact that the primary diamine from which the polyether polyamino methylene phosphonates are prepared by phosphonomethylation may be a mixture of polyethers in which "n" is two or more of 2, 3, 4, 5 and so forth, in varying proportions. For example, a preferred polyether polyamino methylene phosphonate for use in the compositions and methods of the present invention has a molecular weight of approximately 632 and the value of "n" on average is about 2.6. Thus, this type of polyether phosphonate has a molecular weight distribution, i.e., of the various polyoxypropylenes which make it up, and this distribution is represented by a fractional integer average value for "n". But, it is also within the scope of the present invention for "n" to be a whole integer e.g. "3" which usually designates a single molecular weight and not a molecular weight distribution.

The polyether polyamino methylene phosphonate and corresponding N-oxides of the compositions and methods of the present invention are prepared first by phosphonomethylation of the appropriate primary amine which already contains the polyoxyethylene and polyoxypropylene moieties, followed by an oxidation step which provides the N-oxide moieties.

Such primary amine starting materials and their method of preparation are well known. The phosphonomethylation of the primary amine is then carried out by a Mannich reaction such as that described in K. Moedritzer and R. Irani, *J. Organic Chem.* 31(5) 1603-7, "The Direct Synthesis of alpha-Aminomethyl Phosphonic Acids; Mannich-Type Reactions with Orthophosphorous Acid", May 1966. In a typical reaction, the primary amine is added to a mixture of phosphorous acid and water, and concentrated hydrochloric acid is then added slowly, after which the reaction mixture is heated to reflux with addition of aqueous formaldehyde.

Although the general structural formula employed herein indicates that the nitrogen atom is completely phosphonomethylated, as a practical matter, preparation of the polyether polyamino methylene phosphonate and corresponding N-oxides of the present invention, as described in detail further below, usually results in only about 80 to 90% phosphonomethylation. Other side products give N-substitution with H, $CH_3$, $CH_2OH$, etc. It is not practical, as a matter of simple production economics, however, to isolate and purify the completely phosphonomethylated compounds, since the side products just described do not interfere with silica/silicate deposit inhibition. Such side products, are consequently, usually allowed to remain, and the test data set out further below is based on test samples containing such side products. Consequently, the activity levels obtained would be even higher were 100% active compound being tested.

Once the desired phosphonomethylated polyoxypropylene diamine has been prepared as described above, the N-oxide final product of the present invention is then prepared by a step of oxidation, which may be accomplished, e.g., simply by adding hydrogen peroxide to a basic solution of the phosphonomethylated diamine and heating the reaction mixture, which gives high yields of the N-oxide final product. Of course, it is also possible to use other well known techniques for carrying out such a step of oxidation, and any number of these may be successfully employed.

The amounts of any particular polyether polyamino methylene phosphonate that are required to be added for the desired maximum inhibition of silica/silicate deposit formation will be such as to provide an ultimate concentration in the aqueous system being treated of between 0.1 and 50 mg/L, and preferably this concentration will be between 5 and 30 mg/L. Most preferably the concentration will be between 10 and 20 mg/L, although it is understood that many factors, of the type which have been explained in detail with regard to the background to the present invention, will determine the actual amount of polyether phosphonate which will be added to any particular aqueous system in order to achieve the maximum amount of inhibition of silica/silicate deposit formation in that aqueous system. The calculation of those amounts will be well within the skill of the artisan in this field.

It is contemplated to be a part of the present invention to utilize the polyether phosphonates together with one or more of various polymer additives in order to achieve improved performance with respect to inhibiting the deposit of silica/silicate scale. Such polymer additives comprise one or more members selected from the group consisting of: homo- and copolymers including terpolymers comprising one or more of acrylamide (AM), acrylic acid (AA), 2-acrylamide-methyl propane sulfonic acid (AMPSA), methacrylic acid (MAA), iraconic acid (IA), polyethylene glycol monomethacrylate (PGM), maleic anhydride (MA), maleic acid (MA), t-butyl acrylamide (TBAM), sodium styrene sulfonate (SSS), sodium vinyl sulfonate, hydroxy propyl acrylate, hydroxy propyl methacrylate, 3-allyloxy-2-hydroxy propane sulfonic acid, sodium salt (AHPS), and vinyl phosphonic acid, wherein the weight average molecular weight for such polymer additives is in the range of from about 500 to 250,000. In particular, it is preferred that said polymer additive is a member selected from the group consisting essentially of 90/10 to 10/90 AA-/AMPSA, preferably 75/25 and 60/40 AA/AMPSA, 100 AA, 75/25 SSS/MA, 33/33/34 AA/MAA/IA, 50/50 AA/AM, 70/20/10 AA/AMPSA/PGM-5 (having 5 repeating oxyethylene units), and AA/AMPSA/TBAM.

When the polyether polyamino methylene phosphonate used in the methods and compositions of the present invention are used in combination with one or more of the polymers recited further above, the amounts of that combination which must be added in order to inhibit silica/silicate deposition in an aqueous system, will as a general matter be within the ranges of amounts sufficient to establish the ranges of concentrations of the polyether phosphonates and corresponding N-oxides used alone, as recited in detail above. Again, however, calculation of the actual amount is well within the skill of the art.

The manner of addition of any particular polyether polyamino methylene phosphonate to an aqueous system will also be straightforward to a person of ordinary skill in this art. It may be added in finely subdivided solid form by mechanical dispensers of known design. It may also be added in solid form, but in the form of a matrix in which solid particles of the active ingredient are bonded or bound together by a material which is water soluble, or optionally, does not dissolve at all. Such a matrix allows for regular leaching out or dissolving of the active ingredient particles, whereby it is possible to obtain a sustained release and more unvarying concentration of the sodium monofluorophosphate in the water being treated. The particular polyether phosphonate may also be made up in the form of concentrated solutions for dispensing in liquid form from dispensers well known in the art. The polyether phosphonates may also be combined with other chemical treatment agents for dispensing to the aqueous system, and these in combination may be dispensed in solid or liquid form.

The phrase "aqueous system" as used herein is meant to include any system containing water; including, but not limited to, cooling water systems including cooling towers, boiler water systems, desalination systems, gas scrubber units, blast furnaces, sewage sludge dewatering systems, thermal conditioning equipment, reverse osmosis units, sugar evaporators, paper manufacturing systems, mining circuits, and the like.

As used herein, the term "controlling silica/silicate deposition" is meant to include inhibition of silica polymerization, threshold precipitation inhibition, stabilization, dispersion, solubilization, and/or particle size reduction of silica, silicates, especially calcium and magnesium silicates, and silicon ions. Clearly, the instant additives are threshold silicate precipitation inhibitors, but it is believed that they also stabilize, disperse and solubilize silica and silicates. Thus, it has been discovered that polyether polyamino methylene phosphonates, alone or in combination with the polymer additives described above, inhibit, minimize or prevent silica deposition under the severe operating conditions described herein, even though this does not constitute an attempt to describe the specific mechanism by which silica/silicate deposition is prevented or inhibited.

EXAMPLES OF PREFERRED EMBODIMENTS

The following examples demonstrate the effectiveness of the treatment methods of the present invention in preventing silica/silicate scale deposition. These examples are illustrative only, and are not intended to be a limitation of the present invention.

EXAMPLE 1

Prevention of Mixed Calcium Carbonate, Silica/Silicates Deposition

The experimental test procedure was similar to that used for equilibrium studies for waters with high dissolved solids, and further described in J. S. Gill and R. B. Varsanik, DeSalination, 60, (1–8), 1986.

A two-liter polypropylene flask with side arm was filled to the 1500 mL level with makeup water having the composition set out in Table 1 below. The temperature of the makeup water was controlled and maintained by immersing an electrically heated heat-exchanger into the polypropylene flask. A refractive index liquid level sensor was placed in the side arm to maintain a constant volume in the main fask by controlling a solenoid valve on the makeup reservoir. Evaporation was achieved by passing filtered dry air or nitrogen at a regulated and measured rate through a fine fritted Teflon* tube placed at the bottom of the flask. The makeup water was concentrated at various rates by controlling the rate of aeration.

After reaching the desired concentration (cyles of concentration), the cycles were maintained constant for several days. This simulated the operating procedure commonly used in industrial cooling towers. In this case, the makeup water was replaced with distilled water in order to stop further concentration and make it possible to monitor the efficacy of the inhibitor at constant cycles of concentration.

The makeup water composition set out in Table 1 below was selected because it is stable at room temperature and it gives a sufficient induction time to establish the concentration process before any mineral precipitation occurs. The pH of the makeup water was adjusted to 8.5 and was maintained at 9.0 in the main flask during the entire cycling up process. Aliquots were withdrawn at various time intervals, filtered, and analyzed for chloride, calcium, magnesium and silica. The cycles of concentration were determined based on the chloride concentration in the cycled up water. The expected concentration of the other species in solution was then calculated based on the cycles of concentration. The amount of deposit on the heat exchanger was determined by weighing the heat exchanger in the beginning and at the end of the run.

The inhibitors which were evaluated in accordance with the above procedures were as follows:

"A" the polyether phosphonate of the main formula wherein M=H, R=CH3 in all cases, and n =on average about 2.6.

"B" the polyether phosphonate "A" +the polymer additive 70/20/10 AA/AMPSA/PGM-5, having 5 repeating oxyethylene units.

"C" 2-phosphonobutane-1,2,4-tricarboxylic acid (PBTA), commercially available from Mobay as Bayhibit AM.

The results are shown in Table 2 below.

TABLE 1

| COMPOSITION OF THE START-UP AND MAKEUP WATER | | |
|---|---|---|
| | Concentration (mg/L) | |
| Ion | Start-up Water | Makeup Water |
| Silica | 100 | 32 |
| Calcium | 70 | 36 |
| Magnesium | 25 | 9 |
| Bicarbonate | 200 | 80 |
| Sulfate | 98 | 35 |
| Chloride | 124 | 64 |
| Sodium | 157 | 56 |

TABLE 2

| SILICA/SILICATE INHIBITION AT pH 9.0, 6 DAYS CYCLING UP, 6 DAYS CONSTANT CYCLES | | | | | |
|---|---|---|---|---|---|
| | Dosage | % Deposit | % Retention in Solution | | |
| Inhibitor | (mg/L) | Inhibition | SiO2 | Ca | Mg |
| A | 20.0 | 97 | 59 | 79 | 74 |
| B | 167.0 | 99 | 70 | 78 | 80 |
| C | 20.0 | 15 | 79 | 69 | 11 |
| Blank | 20.0 | — | 71 | 62 | 34 |

From the data in Table 2 above, it is clear that polyether phosphonate "A" is very effective in preventing the adherence of deposits of mixed calcium carbonate, silica and silicates on the heated metal surfaces. This is also true for the combination "B" of polyether phosphonate "A" with a polymer additive (70/20/10 AA/AMP-SA/PGM-5). The appearance of the heat exchanger tube for test sample "A" was similar to that of a fresh clean tube with a very light film of scale.

What is claimed is:

1. A method of inhibiting deposition of salt scale including mixed calcium carbonate, silica and/or silicate in an aqueous system selected from the group consisting of recirculating cooling water systems, boiler water systems, reverse osmosis systems, gas scrubbers and evaporators having a pH of at least 8.5 and a calcium saturation level of at least 150 times the solubility limit of calcium as calcite, comprising the step of treating said system with an effective scale-inhibiting amount of a polyether polyamino methylene phosphonate of the following formula:

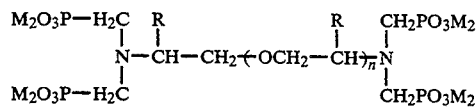

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl.

2. A method according to claim 1 wherein in the above formula for the polyether phosphonate, M is hydrogen, R is methyl, and n is an average of about 2.6.

3. A method according to claim 1 in which the aqueous system being treated is characterized by a pH of at least 9.0 and a calcium saturation level of at least 250 times the solubility limit of calcium as calcite; and the polyether phosphonate is used in an amount sufficient to achieve a concentration of from 0.1 to 50 mg/L in said aqueous system.

4. The method of claim 1 wherein the concentration of polyether phosphonate is from 1.0 to 10 mg/L.

5. A method of inhibiting deposition of salt scale including mixed calcium carbonate, silica and/or silicate in an aqueous system selected from the group consisting of recirculating cooling water systems, boiler water systems, reverse osmosis systems, gas scrubbers and evaporators having a pH of at least 8.5 and a calcium saturation level of at least 150 times the solubility limit of calcium as calcite, comprising the step of treating said system with an effective scale-inhibiting amount of a polyether polyamino methylene phosphonate of the following formula:

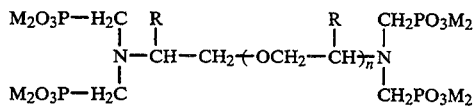

and optionally the N-oxides thereof; where n is an integer or fractional integer which is, or on average is, from about 2 to about 12, inclusive; M is hydrogen or a suitable cation; and each R may be the same or different and is independently selected from hydrogen and methyl;

TOGETHER WITH A POLYMER ADDITIVE COMPRISING:

one or more members selected from the group consisting of: homo- and copolymers including terpolymers comprising one or more of acrylamide (AM), acrylic acid (AA), 2-acrylamide-methyl propane sulfonic acid (AMPSA), methacrylic acid (MAA), itaconic acid (IA), polyethylene glycol monomethacrylate (PGM), maleic anhydride (MAH), maleic acid (MA), t-butyl acrylamide, sodium styrene sulfonate (SSS), sodium vinyl sulfonate, hydroxy propyl acrylate, hydroxy propyl methacrylate, 3-allyloxy-2-hydroxy propane sulfonic acid (AHPS), and vinyl phosphonic acid, wherein the weight average molecular weight for such polymer additives is in the range of from about 500 to 250,000.

6. A method according to claim 5 in which for the above formula for the polyether phosphonate, M is hydrogen, R is methyl, and n is an average of about 2.6; the aqueous system being treated is characterized by a pH of at least 9.0 and a calcium saturation level of at least 250 times the solubility limit of calcium as calcite; the polyether phosphonate is used in an amount sufficient to achieve a concentration of from 0.1 to 50 mg/L in said aqueous system; and said polymer additive is a member selected from the group consisting essentially of 90/10 to 10/90 AA/AMPSA, 100 AA, 75/25 SSS/MA, 33/33/34 AA/MAA/IA, 50/50 AA/AM, 70/20/10 AA/AMPSA/PGM-5 (having 5 repeating oxyethylene units), and AA/AMPSA/TBAM.

7. A method according to claim 6 wherein the polyether phosphonate is used in an amount sufficient to achieve a concentration of from 1.0 to 10 mg/L in said aqueous system.

8. The method according to claim 5 wherein said silica and/or silicate is initially present in said aqueous system at a concentration of at least about 100 mg/L.

* * * * *